United States Patent [19]
Jaffee et al.

[11] Patent Number: 6,033,674
[45] Date of Patent: *Mar. 7, 2000

[54] METHOD OF TREATING CANCER WITH A TUMOR CELL LINE HAVING MODIFIED CYTOKINE EXPRESSION

[75] Inventors: Elizabeth M. Jaffee, Lutherville; Drew M. Pardoll, Brookville; Hyam I. Levitsky, Owings Mills, all of Md.

[73] Assignee: Johns Hopkins University School of Medicine, Baltimore, Md.

[*] Notice: This patent issued on a continued prosecution application filed under 37 CFR 1.53(d), and is subject to the twenty year patent term provisions of 35 U.S.C. 154(a)(2).

[21] Appl. No.: 08/773,367

[22] Filed: Dec. 26, 1996

Related U.S. Application Data

[60] Provisional application No. 60/032,801, Dec. 28, 1995.

[51] Int. Cl.⁷ ............................ A61K 35/39; C07H 21/04
[52] U.S. Cl. .................................. 424/277.1; 424/93.21; 424/93.7; 424/85.1; 435/69.5; 435/70.1; 435/375; 435/384; 435/369; 435/405; 435/406; 536/23.5
[58] Field of Search ............................... 435/172.1, 69.5, 435/405, 70.1, 406, 375, 384, 369; 425/172.1, 69.5, 405, 70.1, 406, 375, 384, 369; 536/23.5

[56] References Cited

U.S. PATENT DOCUMENTS

| | | | |
|---|---|---|---|
| 4,595,653 | 6/1986 | Kronenberg | 435/5 |
| 5,342,774 | 8/1994 | Boon et al. | 435/240.2 |
| 5,399,346 | 3/1995 | Anderson et al. | 424/93.21 |
| 5,637,483 | 6/1997 | Dranoff et al. | |

FOREIGN PATENT DOCUMENTS

| | | |
|---|---|---|
| 0 367 605 A2 | 5/1990 | European Pat. Off. |
| WO 90/11085 | 10/1990 | WIPO |
| WO 92/05262 | 4/1992 | WIPO |
| WO 94/04196 | 3/1994 | WIPO |
| WO 95/31107 | 11/1995 | WIPO |

OTHER PUBLICATIONS

Darrow et al., *J. Immunol.*, 142, 3329–3335 (1989).
Gastl et al., *Cancer Research*, 52, 6229–6236 (1992).
Golumbek et al., *Cancer Research*, 53, 5841–5844 (1993).
Hom et al., *J. Immunother.*, 10, 153–164 (1991).
Huang et al., *Science*, 264, 961–965 (1994).
Itaya et al., *Cancer Research*, 47, 3136–3140 (1987).
Jaffee et al., *Seminars in Oncology*, 22, 81–91 (1995).
Kawakami et al., *J. Immunol.*, 148, 638–643 (1992).
Nabel et al., *Proc. Natl. Acad. Sci. USA*, 90, 11307–11311 (1993).
Ostrand–Rosenberg et al., *Int. J. Cancer: Supplement*, 6, 61–68 (1991).
Plantz et al., Proc. Natl. Acad. Sci. USA, 90, 4645–4649 (1993).
Szuromi (ed.), *Science*, 264, 885 (1994).
Database WPI, Week 7808, Derwent Info Ltd., AN 77–09702Y/06 (JP 53–003–509 abstract), (Jan. 1978).
Database WPI, Week 8928, Derwent Info Ltd., AN 89–206442/28 (WO 89/05631 abstract), (1998).
Database WPI, Week 9035, Derwent Info Ltd., AN 90–266194/35 (JP 2–188–532 abstract), (Jul. 1990).
Database WPI, WEEK 9250, Derwent Info Ltd., AN 92–415476/50 (WO 92/20374 abstract), (1992).
Database WPI, Week 9317, Derwent Info Ltd., AN 93–136183/17 (EP 538,952 abstract), (Apr. 1993).
Database WPI, Weeks 9432 and 9518, Derwent Info Ltd., AN 94–264105/32 (WO 94/17192 abstract), (1994).
Database WPI, Week 9503, Derwent Info Ltd., AN 95–022468/03 (WO 94/27635 abstract), (1994).
Database WPI, Week 9536, Derwent Info Ltd., AN 94/169430/21 (EP 599,077 abstract), (1994).
Jaffee et al., High Efficiency Gene Transfer into Primary Human Tumor Explants without Cell Selection, *Cancer Research*, 53, 2221–2226 (1993).
Kalthoff et al., "Regulation of Tumor Cells by Cytokines," *Contrib. Oncol.*, 50, 101–110 (1995).
Browning et al Cell vol. 72 847–856, Mar. 1993.
Johnson et al Cancer Treatment Review vol. 2 1–31, 1975.
Gura et al Science vol. 278 1041–1042, Nov. 1997.
Ellem et al Cancer Immunol Immunother vol. 44 10–20, 1997.
Paul et al Fundamental Immunology Third Edition Chapter 21 p. 826, 1993.

*Primary Examiner*—Julie Burke
*Attorney, Agent, or Firm*—Leydig, Voit & Mayer, Ltd.

[57] ABSTRACT

The present invention provides a method of treating cancer comprising (a) obtaining a tumor cell line, (b) modifying the tumor cell line to render it capable of producing an increased level of a cytokine relative to the unmodified tumor cell line, and (c) administering the tumor cell line to a mammalian host having at least one tumor that is the same type of tumor as that from which the tumor cell line was obtained, wherein the tumor cell line is allogeneic and is not MHC-matched to the host. The present invention also provides a pancreatic tumor cell line, a method and medium for obtaining such a tumor cell line, and a composition comprised of cells of a purified pancreatic tumor cell line.

17 Claims, No Drawings

METHOD OF TREATING CANCER WITH A TUMOR CELL LINE HAVING MODIFIED CYTOKINE EXPRESSION

This application claims priority to U.S. patent application Ser. No. 60/032,801, which was filed on Dec. 28, 1995, and which has since lapsed.

This invention was made with Government support under Grant Number CA62924 awarded by the National Institutes of Health, and under Grant Number CA57842 awarded jointly by the National Institutes of Health and National Cancer Institute. The Government may have certain rights in this invention.

TECHNICAL FIELD OF THE INVENTION

The present invention pertains to a method of treating cancer using allogeneic tumor cell lines, i.e., tumor cell lines that are genetically dissimilar to those of the host. In particular, the invention pertains to a method of treating pancreatic cancer using an allogeneic pancreatic tumor cell line. The present invention also pertains to a pancreatic tumor cell line, a method and medium for obtaining such a cell line, and a composition comprised of cells of a purified pancreatic tumor cell line.

BACKGROUND OF THE INVENTION

It is generally accepted that human tumor cells contain multiple specific alterations in the cellular genome responsible for their malignant phenotype. These alterations affect the expression or function of genes that control cell growth and differentiation. For instance, typically these mutations are observed in oncogenes, or positive effectors of cellular transformation, such as ras, and in tumor suppressor genes (or recessive oncogenes) encoding negative growth regulators, the loss of function of which results in expression of a transformed phenotype, such as p53, Rb1, DCC, MCC, NF1, and WT1.

Mutations have been detected in all of the common human tumors including pancreatic and colorectal carcinomas. To date, a transforming ras gene (i.e., a mutated version of H-ras, K-ras, or N-ras encoding a protein having an altered amino acid at one of the critical positions 12, 13 and 61) is the oncogene most frequently identified in human cancer. As reviewed by Barbacid, *Ann. Rev. Biochem.*, 56, 779–827 (1987), a ras oncogene has been observed in carcinoma of the bladder, breast, colon, kidney, liver, lung, ovary, pancreas, rectum, and stomach; in hematopoietic tumors of lymphoid and myeloid lineage; in tumors of mesenchymal origin such as fibrosarcomas and rhabdomyosarcomas; and in other tumors, including melanomas, teratocarcinomas, neuroblastomas, and gliomas. In particular, a ras mutation has been identified in greater than 90% of patients with adenocarcinoma of the pancreas, as described by Bos, *Cancer Research*, 49, 4682–4689 (1989).

Tumors of the pancreas are highly malignant and generally result in death. In fact, cancer of the pancreas is the fifth leading cause of cancer-related death in the United States. The presently available treatment modalities have shown little or no benefit for patients with tumors that are unresectable (i.e., regionally advanced or metastatic cancers). Similarly, for patients with localized disease that can be resected, state-of-the-art adjuvant therapy with radiation and chemotherapy has shown only modest benefits—and that at the expense of significant treatment toxicity. Over 71% of cancer patients undergoing adjuvant therapy will eventually die of recurrent disease. For these reasons, more effective treatments are currently needed for cancer, and, in particular, both for advanced as well as limited-stage pancreatic cancer.

Immunotherapy is a potentially therapeutic approach for the treatment of cancer. Immunotherapy is based on the premise that the failure of the immune system to reject spontaneously arising tumors is related to the failure of the immune system to respond appropriately to tumor antigens. In a functioning immune system, tumor antigens are processed and expressed on the cell surface in the context of major histocompatibility complex (MHC) class I and II molecules, which, in humans, also are termed "human-leukocyte associated" (HLA) molecules. When complexed to antigens, the MHC class I and II molecules are recognized by $CD8^+$ and $CD4^+$ T cells, respectively. This recognition generates a set of secondary cellular signals and the paracrine release of specific cytokines, or soluble so-called "biological response modifiers", that mediate interactions between cells and stimulate host defenses to fight off disease. The release of cytokines then results in the proliferation of antigen-specific T cells.

Thus, active immunotherapy involves the injection of is tumor cells, typically in the vicinity of a tumor, to generate either a novel or an enhanced systemic immune response. The ability of this immunotherapeutic approach to augment a systemic T cell response against a tumor has been previously disclosed, e.g., amongst others, see International Application WO 92/05262, Fearon et al., *Cell*, 60, 397–403 (1990), and Dranoff et al., *Proc. Natl. Acad. Sci.*, 90, 3539–3543 (1993). The injected tumor cells are usually altered to enhance their immunogenicity, such as by admixture with non-specific adjuvants, or by genetic modification of the cells to express cytokines, or other immune co-stimulatory molecules. The tumor cells employed can be autologous, i.e., derived from the same host as is being treated. Alternately, the tumor cells can be MHC-matched, or derived from another host having the same, or at least some of the same, MHC complex molecules.

Clinical researchers prefer the use of autologous over MHC-matched tumor cells, and vice versa, for different reasons. Namely, autologous cells are preferred since each patient's tumor expresses a unique set of tumor antigens that can differ from those found on histologically-similar, MHC-matched tumor cells from another patient, see, e.g., Kawakami et al., *J. Immunol.*, 148, 638–643 (1992); Darrow et al., *J. Immunol.*, 142, 3329–3335 (1989); and Hom et al., *J. Immunother.*, 10, 153–164 (1991). Studies evaluating human melanoma antigens confirm that all the human tumor antigens identified to date are shared among at least 50% of patients' tumors—regardless of whether or not the same MHC-type is similarly shared. Use of cells from a patient's own tumor circumvents any need for matching of tumor or MHC antigens.

In comparison, MHC-matched tumor cells are preferred since the use of autologous tumor cell vaccines require that each patient be taken to surgery to obtain a sample of their tumor for vaccine production. The in vitro expansion of fresh human tumor explants necessary for the production of autologous tumor cell vaccines is labor-intensive, technically demanding, and frequently impossible for most histologic types of human tumors, even with highly specialized research facilities. Moreover, the production of a vaccine from each patient's tumor is quite expensive. There also is a substantial likelihood that after extended passage of autologous cells in culture, the antigenic composition of such cells will change relative to the primary tumor from which the cell line originated, making the cells ineffective as a vaccine. While such change is inevitable with all established cell lines, as regarding the use of autologous cells as a tumor vaccine, it will require the maintenance of freezer stocks of each initially-isolated cell line for each patient being treated using this approach.

Based on these shortcomings associated with use of autologous and MHC-matched cells as tumor vaccines, other researchers have sought alternative tumor vaccines, as reviewed by Jaffee et al., *Seminars in Oncology*, 22, 81–91 (1995). The recent results of Huang et al., *Science*, 264, 961–965 (1994), are relevant to this proposal. Namely, prior to this study, tumor vaccine strategies were based on the understanding that the vaccinating tumor cells function as the antigen presenting cells (APCs) that present the tumor antigens on their MHC class I and II molecules, and directly activate the T cell arm of the immune response. In contrast, the results of Huang et al. indicate that the professional APCs of the host rather than the vaccinating tumor cells prime the T cell arm of the immune response. The tumor vaccine cells secrete a cytokine such as GM-CSF and recruit to the region of the tumor bone marrow-derived APCs. The bone marrow-derived APCs take up the whole cellular protein of the tumor for processing, and then present the antigenic peptide(s) on their MHC class I and II molecules. In this fashion, the APCs prime both the $CD4^+$ and the $CD8^+$ T cell arms of the immune system, resulting in the generation of a systemic antitumor immune response that is specific for the antigenic epitopes of the host tumor. These results suggest that it may not be necessary to use autologous or MHC-matched tumor cells in cancer treatment.

Other results suggest that the transfer of allogeneic MHC genes (i.e., genes from a genetically dissimilar individual of the same species) can enhance tumor immunogenicity. Specifically, in certain cases, the rejection of tumors expressing allogeneic MHC class I molecules resulted in enhanced systemic immune responses against subsequent challenge with the unmodified parental tumor, as reviewed in Jaffee et al., supra, and Huang et al., supra. This appears to represent an example of the general phenomenon described as "xenogenization" by Itaya et al., *Cancer Res.*, 47, 3136–3140 (1987), wherein tumor vaccine potency is enhanced by introducing genes into the tumor cell that code for foreign antigens.

Thus, there remains a need for a method of treating cancer, in particular, a method of treating pancreatic cancer, which does not rely on use of autologous or MHC-matched tumor cells, and that avoids the difficulties and shortcomings associated with such use. The present invention provides such a method, as well as components necessary for effectuating the method. These and other objects and advantages of the present invention, as well as additional inventive features, will be apparent from the description of the invention set forth herein.

BRIEF SUMMARY OF THE INVENTION

The present invention provides a method of treating cancer comprising the steps of (a) obtaining a tumor cell line, (b) modifying the tumor cell line to render it capable of producing an increased level of a cytokine relative to the unmodified tumor cell line, and (c) administering the tumor cell line to a mammalian host having at least one tumor that is the same type of tumor as that from which the tumor cell line was obtained. The tumor cell line is allogeneic and is not MHC-matched to the host. In particular, the present invention provides a method of treating pancreatic cancer using an allogeneic pancreatic tumor cell line. The present invention also provides a pancreatic tumor cell line, a method and medium for obtaining such a tumor cell line, and a composition comprised of cells of a purified pancreatic tumor cell line.

DESCRIPTION OF THE PREFERRED EMBODIMENTS

The method of the present invention of treating cancer comprises the steps of (a) obtaining a tumor cell line, (b) modifying the tumor cell line to render it capable of producing an increased level of a cytokine relative to the unmodified tumor cell line, and (c) administering the tumor cell line to a mammalian host having at least one tumor that is the same type of tumor as that from which the tumor cell line was obtained. The administered tumor cell line is allogeneic and is not MHC-matched to the host.

Cancer

The method of the invention can be employed to treat cancer. "Treating cancer" according to the invention comprises administering to a host the tumor cell lines set forth herein for the purpose of effecting a therapeutic response. In particular, a therapeutic response is a systemic immune response (i.e., a T cell response) to tumor antigens. Such a response can be assessed by monitoring the attenuation of tumor growth and/or tumor regression. "Tumor growth" includes an increase in tumor size and/or the number of tumors. "Tumor regression" includes a reduction in tumor mass.

"Cancer" according to the invention includes cancers, in particular those of epithelial origin, characterized by abnormal cellular proliferation and the absence of contact inhibition, which can be evidenced by tumor formation. The term encompasses cancer localized in tumors, as well as cancer not localized in tumors, such as, for instance, cancer cells which expand from a tumor locally by invasion. Thus, any type of cancer can be targeted for treatment according to the invention. For example, the approach preferably can be applied in several clinical scenarios including, but not limited to, local adjuvant therapy for resected cancers, and local control of tumor growth, such as carcinomas of the bladder, breast, colon, kidney, liver, lung, ovary, pancreas, rectum, and stomach. The method also preferably can be used for treatment when the tumor is a sarcoma (e.g., a fibrosarcoma or rhabdosarcoma), a hematopoietic tumor of lymphoid or myeloid lineage, or another tumor, including, but not limited to, a melanoma, teratocarcinoma, neuroblastoma, or glioma.

Preferably the method of the invention can be employed to treat pancreatic cancer. Thus, the present invention also provides a method of treating pancreatic cancer comprising the steps of (a) obtaining a pancreatic tumor cell line, (b) modifying the tumor cell line to render it capable of producing an increased level of a cytokine relative to the unmodified tumor cell line, and (c) administering the tumor cell line to a mammalian host having at least one pancreatic tumor, wherein the tumor cell line is allogeneic and is not MHC-matched to the host.

The method of treating cancer can be effectively carried out using a wide variety of different hosts. For instance, the method can be employed with various eukaryotic hosts, but preferably is employed with mammalian hosts including but not limited to rodent, ape, chimpanzee, feline, canine, ungulate (such as ruminant or swine), as well as, in particular, human hosts.

Tumor Cell Line

As described herein, a "tumor cell line" comprises cells that initially derived from a tumor. Such cells typically have undergone some change in vivo such that they theoretically have indefinite growth in culture; i.e., unlike primary cells, which can be cultured only for a finite period of time. Moreover, such cells preferably can form tumors after they are injected into susceptible animals.

According to the invention, a tumor cell line can be derived from any tumor, e.g., a carcinoma of the bladder, breast, colon, kidney, liver, lung, ovary, pancreas, rectum, and stomach; a hematopoietic tumor of lymphoid or myeloid lineage; a tumor of mesenchymal origin such as a fibrosarcoma or rhabdomyosarcoma; or another tumor, including a melanoma, teratocarcinoma, neuroblastoma, or glioma. Preferably the tumor cell line is derived from a pancreatic tumor.

A tumor cell line employed in a method of treating cancer can be obtained by any suitable means but preferably is obtained in a general method involving the steps of (a) obtaining a sample of a tumor from a mammalian host, (b) forming a single cell suspension from the tumor sample, (c) pelleting the tumor cells, and (d) plating the tumor cells.

More specifically, a sample of a tumor typically can be obtained at the time of surgery. The tumor sample subsequently can be handled and manipulated using sterile technique and in such a fashion so as to minimize tissue damage. The tissue sample can be placed on ice in a sterile container and moved to a laboratory laminar flow hood. The portion of the tumor to be employed for isolation of tumor cell lines can be minced into small pieces; the remainder of the tumor can be stored at −70° C. The slices of tumor then can be digested into single cell suspensions using a solution of Collagenase I. This digestion can be carried out at room or at elevated temperature. Preferably the digestion is carried out at 37° C., while shaking the mixture, e.g., in a shaking incubator.

The single cell suspension is then pelleted, and the pellets can be resuspended in a small volume of tissue culture medium. The resuspended cells can be inoculated into tissue culture medium appropriate for the growth of the cells in culture at a density of about $2 \times 10^5$ tumor cells/ml. Preferably the medium is one that has wide applicability for supporting growth of many types of cell cultures, such as a medium that utilizes a bicarbonate buffering system and various amino acids and vitamins. Optimally the medium is RPMI-1640 medium. The medium can contain various additional factors as necessary, e.g., when required for the growth of tumor cells, or for maintenance of the tumor cells in an undifferentiated state.

The cultures can be maintained at about 35–40° C. in the presence of about 5–7% $CO_2$. The tumor cell cultures can be fed and recultured as necessary, i.e., typically every 1 to 10 days. The tumor cells also can be subjected to differential trypsinization to remove other cells (e.g. stromal cells) that can overgrow the primary tumor cultures. Preferably, such differential trypsinization is done about every 5 to 10 days.

When it appears that a substantially pure culture of the tumor cells has been obtained, various tests can be carried out as necessary to determine the relative purity of the cultures, and to characterize the resultant tumor cell lines. For instance, the existence of certain genetic sequences in the cell line, or certain phenotypic traits, as further described herein, can be explored.

The method of isolating a tumor cell line preferably can be employed for the isolation of a pancreatic tumor cell line. Such a pancreatic tumor cell line similarly can be employed in a method of treating pancreatic cancer and can be obtained by (a) obtaining a sample of a pancreatic tumor from a mammalian host, (b) forming a single cell suspension from the tumor sample, (c) pelleting the tumor cells, and (d) plating the tumor cells. Thus, the present invention provides a substantially purified tumor cell line, particularly a substantially purified pancreatic tumor cell line.

Desirably, as part of the isolation process, the pancreatic tumor cells are plated in a growth medium optimized for culturing pancreatic tumor cells. Preferably this medium is RPMI-1640 medium. Optimally, this medium further comprises fetal serum, insulin, and insulin-like growth factors 1 and 2. Preferably fetal serum is fetal bovine serum and is included at a concentration of about 5 to about 30%, even more preferably, about 10 to about 25%, and optimally, about 20%. Also, preferably insulin is human insulin, and is included in the medium at a concentration of from about 0.02 to about 2.0 U/ml, even more preferably, from about 0.1 to about 1.0 U/ml, and optimally, about 0.2 U/ml. Insulin-like growth factors 1 and 2 can each preferably be included in the medium at a concentration of from about 0.001 to about 0.1 μg/ml, even more preferably, from about 0.005 to about 0.05 μg/ml, and optimally, about 0.01 μg/ml.

The medium and medium components are readily available, and can be obtained, for instance, from commercial suppliers. Such commercial suppliers include, but are not limited to, JRH Biosciences (Lenexa, Kans.), Gibco BRL (Gaithersberg, Md.), Hyclone Labs. (Logan, Utah), Sigma Biosciences (St. Louis, Mo.), Cell Sys. Corp. (Kirkland, Wash.), Intergen Co. (Purchase, N.Y.), Eli Lilly and Co. (Indianapolis, Ind.), Biofluids, Inc. (Rockville, Md.), and other suppliers manufacturing similar products.

Preferably the tumor cell line (which desirably is a pancreatic tumor cell line) comprises a mutation in an oncogene or tumor suppressor gene such that the oncogenic nature of the tumor cell line, and its derivation from a host tumor, can be confirmed. The mutation can occur in any oncogene or tumor suppressor gene, including, but not limited to, trk, ks3, hst, ras, myc, p53, mas, Rb1, DCC, MCC, NF1, and WT1. Optimally the tumor cell line comprises a ras mutation. Preferably the mutation is present in codon 12, 13, or 61 of one of the ras genes H-ras, K-ras, and N-ras. Optimally the mutation is in codon 12 of a ras gene, preferably codon 12 of a K-ras gene.

The use of a tumor cell line characterized by a ras mutation is advantageous inasmuch as the mutations which render a ras gene oncogenic have been characterized, e.g., as reviewed by Bos, supra, and Barbacid, supra. This means that peptides that incorporate amino acid changes known to result in a ras oncoprotein can be synthesized easily, and can be evaluated as targets of cytotoxic T lymphocytes (CTLs). Host immune responses to these peptides can be assessed both before and after vaccination.

The tumor cell line, which preferably is a pancreatic cell line, also can be characterized by a further trait which distinguishes the tumor cells from other cells and can be employed, for instance, for monitoring cell survival either in vittro or in vivo. Examples of such a trait include antibody staining for a particular protein, which, desirably is a cell surface protein. Preferably, the pancreatic tumor cell lines of the present invention demonstrate cytokeratin staining upon histochemical staining using an antibody directed against cytokeratin. Accordingly, the present invention provides preferred pancreatic tumor cell lines including, but not limited to Panc 4.14.93, Panc 1.28.94, Panc 6.3.94, Panc 8.13.94, Panc 9.6.94, Panc 12.1.94, Panc 2.3.95, Panc 4.3.95, Panc 4.21.95, Panc 5.4.95, and, in particular, Panc 10.5.92.

Cytokine

In the method of treating cancer of the invention, preferably the tumor cell line (e.g., the pancreatic tumor cell line)

has been modified to render the tumor cell line capable of producing an increased level of a cytokine relative to the unmodified tumor cell line, or the parental tumor cell line from which the modified tumor cell line derives. A "cytokine" is, as that term is understood by one skilled in the art, any immunopotentiating protein (including a modified protein such as a glycoprotein) that enhances responsiveness of a host immune system to a tumor present in the host. Preferably the cytokine is not itself immunogenic to the host, and potentiates immunity by activating or enhancing the activity of cells of the immune system.

As used herein, a cytokine includes such proteins as interferons (e.g., $IFN_\alpha$, $IFN_\beta$, and $IFN_\gamma$), interleukins (e.g., IL-1 to IL-11), tumor necrosis factors (e.g., $TNF_\alpha$ and $TNF_\beta$), erythropoietin (EPO), macrophage colony stimulating factor (M-CSF), granulocyte colony stimulating factor (G-CSF) and granulocyte-macrophage colony stimulating factor (GM-CSF). Preferably the cytokine is GM-CSF from any source, optimally the cytokine is murine or human GM-CSF.

"Modifying" a tumor cell line according to the invention comprises providing to the tumor cell line a vector capable of imparting increased expression of a cytokine of interest. A "vector" encompasses a DNA molecule such as a plasmid, virus or other vehicle, which contains one or more heterologous or recombinant DNA sequences, e.g., a cytokine gene or cytokine coding sequence of interest under the control of a functional promoter and possibly also an enhancer, and that is capable of functioning as a vector as that term is understood by those of ordinary skill in the art. Appropriate viral vectors include, but are not limited to simian virus 40, bovine papilloma virus, Epstein-Barr virus, adenovirus, herpes virus, vaccinia virus, Moloney murine leukemia virus, Harvey murine sarcoma virus, murine mammary tumor virus, and Rous sarcoma virus.

Reference to a vector or other DNA sequences as "recombinant" merely acknowledges the linkage of DNA sequences which are not typically conjoined as isolated from nature. A "gene" is any nucleic acid sequence coding for a protein or a nascent mRNA molecule. Whereas a gene comprises coding sequences plus any non-coding (e.g., regulatory sequences), a "coding sequence" does not include any non-coding DNA. A "promoter" is a DNA sequence that directs the binding of RNA polymerase and thereby promotes RNA synthesis. "Enhancers" are cis-acting elements of DNA that stimulate or inhibit transcription of adjacent genes. An enhancer that inhibits transcription also is termed a "silencer". Enhancers differ from DNA-binding sites for sequence-specific DNA binding proteins found only in the promoter (which also are termed "promoter elements") in that enhancers can function in either orientation, and over distances of up to several kilobase pairs (kb), even from a position downstream of a transcribed region.

Any suitable vector can be employed that is appropriate for introduction of nucleic acids into eukaryotic tumor cells, or more particularly animal tumor cells, such as mammalian, e.g., human, tumor cells. Preferably the vector is compatible with the tumor cell, e.g., is capable of imparting expression of the cytokine gene or coding sequence, and is stably maintained or relatively stably maintained in the tumor cell. Desirably the vector comprises an origin of replication. Preferably the vector also comprises a so-called "marker" function by which the vector can be identified and selected (e.g., an antibiotic resistance gene). When a cytokine coding sequence is transferred (i.e., as opposed to a cytokine gene having its own promoter), optimally the vector also contains a promoter that is capable of driving expression of the coding sequence and that is operably linked to the coding sequence. A coding sequence is "operably linked" to a promoter (e.g., when both the coding sequence and the promoter together constitute a native or recombinant cytokine gene) when the promoter is capable of directing transcription of the coding sequence.

As used herein, cytokine "gene" or "coding sequence" includes cytokine genomic or cDNA sequences, greater and lesser sequences and mutations thereof, whether isolated from nature or synthesized in whole or in part, as long as the gene or coding sequence is capable of expressing or capable of being expressed into a protein having the characteristic function of the cytokine, i.e., the ability to stimulate the host immune response. The means of modifying genes or coding sequences are well known in the art, and can also be accomplished by means of commercially available kits (e.g., New England Biolabs, Inc., Beverly, Md.; Clontech, Palo Alto, Calif.). The cytokine gene or coding sequence can be of any suitable source, for example, isolated from any mammalian species such as human. Preferably, however, the cytokine gene or coding sequence comprises a GM-CSF sequence, particularly a human or murine GM-CSF gene or coding sequence including a human or murine GM-CSF cDNA sequence (e.g., as described by Cantrell et al., *Proc. Natl. Acad. Sci.*, 82, 6250–6254 (1985)).

In the recombinant vectors of the present invention, preferably all proper transcription, translation and processing signals (e.g., splicing and polyadenylation signals) are correctly arranged on the vector such that the cytokine gene or coding sequence will be appropriately transcribed and translated in the tumor cells into which it is introduced. The manipulation of such signals to ensure appropriate expression in host cells is well within the knowledge and expertise of the ordinary skilled artisan.

Whereas a cytokine gene is controlled by (i.e., operably linked to) its own promoter, another promoter, including a constitutive promoter, such as, for instance the adenoviral type 2 (Ad2) or type 5 (Ad5) major late promoter (MLP) and tripartite leader, the cytomegalovirus (CMV) immediate early promoter/enhancer, the Rous sarcoma virus long terminal repeat (RSV-LTR), and others, can be employed to command expression of the cytokine coding sequence.

Alternately, a tissue-specific promoter (i.e., a promoter that is preferentially activated in a given tissue and results in expression of a gene product in the tissue where activated) can be used in the vector. Such promoters include but are not limited to the elastase I gene control region which is active in pancreatic acinar cells as described by Swift et al., *Cell*, 38, 639–646 (1984) and MacDonald, *Hepatology*, 7, 425–515 (1987); the insulin gene control region which is active in pancreatic beta cells as described by Hanahan, *Nature*, 315, 115–122 (1985); the hepatocyte-specific promoter for albumin or $\alpha_1$-antitrypsin described by Frain et al., *Mol. Cell. Biol.*, 10, 991–999 (1990) and Ciliberto et al., *Cell*, 41, 531–540 (1985); and the albumin and $alpha_1$-antitrypsin gene control regions which are both active in liver as described by Pinkert et al., *Genes and Devel.*, 1, 268–276 (1987) and Kelsey et al, *Genes and Devel.*, 1, 161–171 (1987).

Similarly, a tumor-specific promoter, such as the carcinoembryonic antigen for colon carcinoma described by Schrewe et al., *Mol. Cell Biol.*, 10, 2738–2748 (1990), can be used in the vector. Along the same lines, promoters that are selectively activated at different developmental stages (e.g., globin genes are differentially transcribed in embryos and adults) can be employed for gene therapy of certain types of cancer.

Another option is to use an inducible promoter, such as the IL-8 promoter, which is responsive to TNF, or the 6–16 promoter, which is responsive to interferons, or to use other similar promoters responsive to other cytokines or other factors present in a host or that can be administered exogenously. Use of a cytokine-inducible promoter has the added advantage of allowing for auto-inducible expression of a cytokine gene. According to the invention, any promoter can be altered by mutagenesis, so long as it has the desired binding capability and promoter strength.

Accordingly, the present invention provides a vector that comprises a nucleic acid sequence encoding a cytokine as defined above, and that can be employed in the method of the present invention of treating cancer. In particular, the present invention provides a recombinant vector comprising a nucleic acid sequence encoding GM-CSF. Thus, preferably, the present invention provides the vector designated as pcDNA 1/Neo, which is further described herein.

In the method of the present invention, the recombinant vector can be employed to transfer a cytokine gene or coding sequence to a cell in vitro, which preferably is a cell of an established tumor cell line, particularly, a pancreatic tumor cell line. Various methods can be employed for delivering a vector to cells in vitro. For instance, such methods include electroporation, membrane fusion with liposomes, high velocity bombardment with DNA-coated microprojectiles, incubation with calcium phosphate-DNA precipitate, DEAE-dextran mediated transfection, infection with modified viral nucleic acids, direct microinjection into single cells, and the like. Other methods are available and are known to those skilled in the art. Thus, the present invention provides a substantially purified tumor cell line wherein the cell line has been modified to render it capable of producing an increased level of a cytokine (preferably GM-CSF) relative to the unmodified tumor cell line.

The level of cytokine produced by the modified tumor cell is important in the context of the present invention for the purpose of obtaining an immunostimulatory response. Preferably the modified (e.g., transfected or transformed) tumor cell line produces a level of cytokine that is increased over that observed for the unmodified (i.e., parental) tumor cell line. Even more preferably, the modified cell line produces a level of cytokine that results in cytokine secretion greater than 35 ng/$10^6$ cells/24 hours.

Administering the Modified Tumor Cell Line

"Administering" modified cells of the tumor cell line to a mammalian host refers to the actual physical introduction of the modified (i.e., cytokine-producing) tumor cells into the host. Any and all methods of introducing the modified tumor cells into the host are contemplated according to the invention; the method is not dependent on any particular means of introduction and is not to be so construed. Means of introduction are well known to those skilled in the art, and also are exemplified herein.

Preferably, the modified tumor cell line is administered to a host having at least one tumor (i.e., the host can have more than one tumor) that is of the same type as that from which the cell line was obtained. "Same type of tumor" encompasses tumors that are histologically similar, i.e., similar in terms of the structure and property of the tissue/organ being treated. While it is anticipated that the administered tumor cell line can have some antigens (e.g., tumor antigens or MHC antigens) in common with the host tumor, for the purpose of this invention, it is not necessary that the administered tumor cell and the host tumor have any MHC antigens in common. Similarly, even though tumor antigens can differ between the administered tumor cell line and the host tumor, it is preferred that there is enough commonality such that administration of the tumor cell line can effect a systemic (i.e., a T cell-mediated) response against the host tumor. Accordingly, the present invention encompasses the administration of a tumor cell line, which is allogeneic (i.e., genetically dissimilar) to the host, and which is not MHC-matched to the host. According to this invention a tumor cell line is "not MHC-matched" to a host when it doesn't share any MHC antigens in common with the host, or when it doesn't share any of the MHC antigens with the host which are typically MHC-matched when using tumor cell vaccines (e.g., MHC class I antigens, especially HLA-A2).

Inasmuch as the present invention provides for paracrine delivery of cytokines to tumors in vivo, preferably the genetically modified tumor cell line (e.g., the modified pancreatic tumor cell line) is administered in close proximity to the tumor to be treated. By "close proximity" is meant a distance such that the cytokine released by the modified tumor cell is able to exert its therapeutic effect upon a host cell tumor. Optimally, the modified tumor cell line is not injected directly into the tumor itself.

Also, preferably the modified tumor cell line (e.g., the modified pancreatic tumor cell line) is irradiated prior to administration to prevent cell replication, and possible tumor formation in vivo. For irradiation of tumor cells, the tumor cells typically are plated in a tissue culture plate and irradiated at room temperature using a $^{137}$Cs source. Preferably, the cells are irradiated at a dose rate of from about 50 to about 200 rads/min, even more preferably, from about 120 to about 140 rads/min. Preferably, the cells are irradiated with a total dose sufficient to inhibit the majority of cells, i.e., preferably about 100% of the cells, from proliferating in vitro. Thus, desirably the cells are irradiated with a total dose of from about 10,000 to 20,000 rads, optimally, with about 15,000 rads.

Moreover, the modified tumor cell line (e.g., the transfected pancreatic tumor cell line) optimally is treated prior to administration to enhance its immunogenicity. Preferably, this treatment comprises, as described herein, further genetic manipulation, such as, for instance, introduction of other cytokine or immune co-stimulatory functions, or, for example, admixture with nonspecific adjuvants including but not limited to Freund's complete or incomplete adjuvant, emulsions comprised of bacterial and mycobacterial cell wall components, and the like.

Methods of Use

The allogeneic tumor cell lines, particularly the allogeneic pancreatic tumor cell lines, can be used to vaccinate patients with histologically similar tumors for the purpose of generating a systemic antitumor immune response against the patient's own tumor.

To facilitate administration, a modified allogeneic tumor cell line (i.e, a modified allogeneic pancreatic tumor cell line) can be made into a pharmaceutical composition or implant appropriate for administration in vivo, with appropriate carriers or diluents, which further can be pharmaceutically acceptable. The means of making such a composition or an implant have been described in the art (see for instance, *Remington's Pharmaceutical Sciences*, 16th Ed., Mack, ed. (1980)). Where appropriate, a tumor cell line can be formulated into a preparation in solid, semisolid, liquid or gaseous form, such as a tablet, capsule, powder, granule, ointment, solution, suppository, injection, inhalant, or aerosol, in the usual ways for their respective route of administration. Means known in the art can be utilized to prevent or minimize release and absorption of the composition until it reaches the target tissue or organ, or to ensure timed-release of the composition. Preferably, however, a pharmaceutically acceptable form is employed which does not ineffectuate the compositions of the present invention. Thus, desirably a modified allogeneic tumor cell line (i.e., a modified allogeneic pancreatic tumor cell line) can be made into a pharmaceutical composition comprising a balanced salt solution, preferably Hanks' balanced salt solution.

Thus, the present invention provides a pharmaceutical composition comprising a pharmaceutically acceptable carrier and a tumor cell line. Preferably, the invention provides a pharmaceutical composition comprising a pharmaceutically acceptable carrier and a pancreatic tumor cell line, particularly wherein the tumor cell line is Panc 10.5.92, and especially wherein the tumor cell line, such as Panc 10.5.92, has been modified to produce an increased level of a cytokine, optimally GM-CSF.

In pharmaceutical dosage form, a composition can be used alone or in appropriate association, as well as in combination, with other pharmaceutically active compounds and methods of treatment. For example, in applying a method of the present invention for the treatment of cancer, in particular, for the treatment of pancreatic cancer, such treatment can be employed in conjunction with other means of treatment of cancer, particularly pancreatic cancer, e.g., surgical ablation, irradiation, chemotherapy, and the like.

A pharmaceutical composition of the present invention can be delivered via various routes and to various sites in a mammalian, particularly human, body to achieve a particular effect. One skilled in the art will recognize that, although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration. Preferably, delivery can be accomplished by intradermal administration.

A composition of the present invention can be provided in unit dosage form, wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and animal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the novel unit dosage forms of the present invention depend on the particular pharmacodynamics associated with the pharmaceutical composition in the particular host.

Preferably, a sufficient number of the modified tumor cells are present in the composition and introduced into the host, such that expression of cytokine by the host cell and subsequent recruitment of APCs to the tumor site result in a greater immune response to the extant host tumor than would otherwise result in the absence of such treatment, as further discussed herein. Accordingly, the amount of host cells administered should take into account the route of administration and should be such that a sufficient number of the tumor cells will be introduced so as to achieve the desired therapeutic (i.e., immunopotentiating) response. Furthermore, the amounts of each active agent included in the compositions described herein (e.g., the amount per each cell to be contacted or the amount per certain body weight) can vary in different applications. In general, the concentration of modified tumor cells preferably should be sufficient to provide at least from about $1 \times 10^6$ to about $1 \times 10^9$ tumor cells, even more preferably, from about $1 \times 10^7$ to about $5 \times 10^8$ tumor cells, although any suitable amount can be utilized either above, e.g., greater than $5 \times 10^8$ cells, or below, e.g., less than $1 \times 10^7$ cells.

These values provide general guidance of the range of each component to be utilized by the practitioner upon optimizing the method of the present invention for practice of the invention. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on interindividual differences in pharmacokinetics, drug disposition, and metabolism. One skilled in the art readily can make any necessary adjustments in accordance with the exigencies of the particular situation. Moreover, the effective amount of the compositions can be further approximated through analogy to other compounds known to inhibit the growth of cancer cells, in particular, pancreatic cancer cells.

One skilled in the art also is aware of means to monitor a therapeutic (i.e., systemic immune) response upon administering a composition of the present invention. In particular, the therapeutic response can be assessed by monitoring attenuation of tumor growth, and/or tumor regression. The attenuation of tumor growth or tumor regression in response to treatment can be monitored using several end-points known to those skilled in the art including, for instance, number of tumors, tumor mass or size, or reduction/prevention of metastasis. These described methods are by no means all-inclusive, and further methods to suit the specific application will be apparent to the ordinary skilled artisan.

EXAMPLES

The following examples further illustrate the present invention but, of course, should not be construed as in any way limiting its scope.

Example 1

This example illustrates the method of obtaining and culturing the allogeneic tumor cell lines of the present invention.

Eleven allogeneic pancreatic tumor cell lines were developed from patients undergoing pancreaticoduodenectomy at Johns Hopkins Hospital. These cell lines were generated from fresh human pancreatic tumor explants obtained at the time of surgical resection. Namely, immediately upon tumor resection, the specimen was placed on ice in a sterile container and moved to a laminar flow tissue culture hood in a laboratory. All subsequent manipulations were performed using standard sterile tissue culture technique, and using media and reagents from various commercial suppliers (e.g. JRH Biosciences (Lenexa, Kans.), Gibco BRL (Gaithersberg, Md.), Hyclone Labs. (Logan, Utah), Sigma Biosciences (St. Louis, Mo.), Cell Sys. Corp. (Kirkland, Wash.), Intergen Co. (Purchase, N.Y.), Eli Lilly and Co. (Indianapolis, Ind.), Biofluids, Inc. (Rockville, Md.), and other suppliers manufacturing similar products).

The portion of the tumor to be employed for isolation of tumor cell lines was minced into small pieces measuring about a few millimeters in diameter. The pieces were placed in a solution containing about 15 mg of Collagenase I, and were digested at 37° C. in a shaking incubator into single cell suspensions. The pancreatic tumor cell suspensions were then subjected to gravity centrifugation for five minutes to pellet the cells. The pellets were resuspended and plated by inoculating into a 25 cm² tissue culture flask with about 1–2×10⁶ viable cells in RPMI 1640 medium containing 20% fetal bovine serum, 100 units (U) of human insulin per 500 ml of medium, and 5 µg per 500 ml of medium of each of the insulin-like growth factors 1 and 2. The cultures were placed in 25 cm² tissue culture flasks and were incubated at about 37° C. in humidified incubators with about 5–7% $CO_2$.

Primary cell cultures were subjected every 5 to 10 days to differential trypsinization to remove the majority of stromal cells that routinely overgrow primary pancreatic tumor cultures. Several tests were used to characterize the resultant tumor cell lines and to assess the presence of the malignant epithelial cells as compared with stromal cells and nonmalignant epithelial cells. Namely, histochemical staining was performed using antibodies directed against cytokeratin to distinguish cells of epithelial origin from cells of mesenchymal origin. All of the obtained eleven tumor cell lines were characterized by cytokeratin staining as comprised primarily or exclusively of epithelial cells, as set out in Table 1.

TABLE 1

Cytokeratin Staining of Pancreatic Cell Lines

| | % Cytokeratin positive* | raw Mutation |
|---|---|---|
| Panc 10.5.92 | 100% | codon 12 |
| Panc 4.14.93 | 100% | codon 13 |
| Panc 1.28.94 | 100% | codon 12 |
| Panc 6.3.94 | 100% | codon 12 |
| Panc 8.13.94 | 100% | codon 12 |
| Panc 9.6.94 | 100% | codon 12 |
| Panc 12.1.94 | 100% | codon 12 |
| Panc 2.3.95 | 100% | codon 12 |
| Panc 4.3.95 | 100% | codon 12 |
| Panc 4.21.95 | 100% | codon 12 |
| Panc 5.4.95 | 100% | codon 12 |

*Cytokeratins 7 and 18

Also, all generated tumor cell lines were evaluated for maintenance of the same ras mutation that was observed in the original tumor specimen prior to in vitro culture to validate the malignant origin of the cell line, as well as the genetic stability of the cell line in culture. As illustrated in Table 1, all of these lines were confirmed to have a ras mutation identical to that of the original tumor from which the tumor cell line derived. Codon 12 mutations present in the tumor cell lines resulted in a Asp→Gly conversion, and codon 13 modifications resulted in a Ser→Gly conversion in the encoded Ras oncoprotein. In addition, all tumor cell lines were observed to express high levels of MHC class I antigens. Two of the four lines (i.e., Panc 10.5.92 and Panc 9.6.94) also express elevated levels of MHC class II antigens. The pancreatic tumor cell lines are easily expanded in culture and have doubling times of about 72 hours.

The methods employed in this example for derivation of allogeneic pancreatic tumor cell lines similarly can be employed for the generation and isolation of other kinds of allogeneic tumor cell lines.

Example 2

This example illustrates the method of modifying the allogeneic tumor cell lines of the present invention to produce an increased amount of a cytokine. Inasmuch as the cytokine granulocyte-macrophage colony stimulating factor (GM-CSF) is potentially more potent than other cytokines in generating a systemic antitumor response in preclinical tumor models (Dranoff et al., Proc. Natl. Acad. Sci., 90, 3539–3542 (1993), the Panc cell line 10.5.92 described in Example 1 was employed as representative of the allogeneic tumor cell lines, and was modified to secrete GM-CSF.

To accomplish this, a recombinant human GM-CSF gene was cloned into pcDNA 1/Neo. All cloning reactions and DNA manipulations were carried out using methods well known to the ordinary skilled artisan, and which have been described in the art, e.g., Maniatis et al., Molecular Cloning: A Laboratory Manual, 2nd ed. (Cold Spring Harbor Laboratory, NY, (1982)). Enzymes employed in these reactions were obtained from commercial suppliers (e.g., New England Biolabs, Inc., Beverly, Mass.; Clontech, Palo Alto, Calif.; Boehringer Mannheim, Inc., Indianapolis, Ind.; etc.) and were used according to the manufacturers' recommendations.

The plasmid pcDNA 1/Neo contains the human GM-CSF cytokine coding sequence under the control of the cytomegalovirus (CMV) promoter, and the neomycin resistance gene also controlled by a separate CMV promoter. The CMV promoter was employed since it is able to drive a relatively high level of gene expression in most eukaryotic cells (Boshart et al., Cell, 41, 521–530 (1985)). Initial studies using this vector for gene transfer to a human melanoma cell line confirm that, following selection for neomycin resistance, secreted levels of GM-CSF greater than 35 ng/$10^6$ cells/24 hours were achieved. These initial studies indicate that the pcDNA 1/Neo plasmid is functional. Moreover, this is the dose of GM-CSF that is required to generate adequate antitumor immune responses in mouse models. Namely, dilution experiments using varying concentrations of tumor cells that either were or were not transduced with a retroviral vector carrying a GM-CSF gene confirm that in the B16-F10 tumor system, GM-CSF secretion below 35 ng/$10^6$ cells/24 hours fails to generate the potent antitumor immunity seen at levels of secretion above this threshold. These findings underscore the importance of delivering high and sustained levels of GM-CSF directly at the site of the vaccinating tumor cells that are the source of the relevant tumor antigen.

The Panc line 10.5.92 was transfected with pcDNA 1/Neo by electroporation, and was subsequently cloned by limiting dilution. GM-CSF levels were determined by ELISA and confirmed by bioassay using GM-CSF dependent TF-1 cells (Kitamura et al., Blood, 73, 375–380 (1989)). The GM-CSF secretion level observed for the resultant transfected pancreatic tumor cell line is about 90 ng/$10^6$ tumor cells/24 hours. Irradiation of the transfected tumor cells prevents their replication, but allows the cells to secrete GM-CSF and to remain metabolically active for up to one week in culture. Irradiation was carried out using a $^{137}$Cs source at a dose rate of about 120–140 rads/min to deliver a total dose of about 15,000 rads.

The methods employed in this example also can be used to generate other tumor cell lines capable of producing increased amounts of cytokine, and which similarly can be employed as vaccines.

Example 3

This example illustrates further studies regarding GM-CSF administration to a host.

Further studies confirm that GM-CSF secretion needs to parallel the known paracrine physiology of this cytokine. In particular, secretion must be at the site of the relevant antigens (i.e., the tumor cells), as described in the previous example, and high levels must be sustained for several days (Dranoff et al., supra; Golumbek et al., *Cancer Research*, 53, 1–4 (1993)). However, it appears that the tumor cell, itself, need not be the source of GM-CSF secretion (Golumbek et al., supra). Immunologic protection and histologic infiltrates similar to those seen with retrovirally transduced cytokine-expressing tumor cells can be generated when GM-CSF is slowly released from biodegradable polymers co-injected with the tumor cell. In addition, if a second non-cross-reacting tumor is co-injected with a GM-CSF-secreting tumor, immunologic protection against both tumors can be generated. Simple injection of soluble GM-CSF along with tumor cells, however, does not provide sustained local levels of this cytokine and does not generate systemic immunity (Golumbek et al., supra). Thus, the effectiveness of using an allogeneic tumor cell that was not MHC-matched to the host cell for delivery of cytokine in vivo was explored.

In murine models, it was demonstrated that the antitumor immunity generated with the delivery of GM-CSF by bystander allogeneic tumor cells is comparable to that achieved when GM-CSF is delivered by the target tumor cell itself. Specifically, in these experiments, BALB/c mice were subcutaneously vaccinated with irradiated CT26 colon carcinoma cells, with GM-CSF delivered either by retrovirally transduced CT26 cells, or by retrovirally transduced B16-F10 cells. Two weeks later, mice were rechallenged with injections of wild-type strain CT26. The CT26 tumor cell line possesses some intrinsic immunogenicity; however, a greater degree of protection was seen when GM-CSF was secreted at the vaccination site, whether by the syngeneic or the allogeneic tumors. While it is unclear to what degree, or by what mechanism, the allogeneic tumor cells can augment antitumor immunity, these data strongly suggest that allogeneic delivery of GM-CSF is likely to be at least as effective as autologous tumor delivery.

Example 4

This example illustrates the method of treating cancer by administering to a host the genetically modified allogeneic tumor cell lines of the present invention.

Tumor cell lines that secrete levels of GM-CSF greater than 35 ng/$10^6$ tumor cells/24 hours are obtained and employed. The modified tumor cells are harvested from the tissue culture flasks by trypsinization. The cells are washed using normal saline, pelleted, and resuspended in Hanks' balanced salt solution, or some other salt solution appropriate for introduction in vivo. The cells are resuspended at a concentration of from about $1 \times 10^7$ to about $1 \times 10^{10}$ tumor cells/ml, and optimally, at a concentration of from about $1 \times 10^8$ to about $5 \times 10^9$ tumor cells/ml. About 0.1 ml of this resuspension mixture is employed as a vaccine. Thus, preferably from about $1 \times 10^6$ to about $1 \times 10^9$ tumor cells are injected, and optimally, from about $1 \times 10^7$ to about $5 \times 10^8$ tumor cells are injected in toto. Whereas the modified tumor cells are injected subcutaneously in the mouse, the cells preferably are injected intradermally in humans. Injections preferably are made in the vicinity of the tumor; optimally, the vaccines are not injected directly into the tumor, itself. Also, the amounts of tumor cells employed for vaccination in humans are roughly about ten times greater than the amounts employed for vaccination in the mouse.

Prior to injection, the modified tumor cells can be irradiated e.g., using a $^{137}$Cs source as described in Example 2, to prevent replication of the modified tumor cells in vivo. The modified tumor cells also can be altered to enhance their immunogenicity. For instance, the cells can be further genetically manipulated (e.g., through insertion of other cytokine or immune stimulatory nucleic acid sequences), or can be admixed with non-specific adjuvants (e.g., Freund's complete or incomplete adjuvant, emulsions comprised of bacterial and mycobacterial cell wall components, etc.).

The invention can be used in mammals, particularly humans, having various tumors, for instance, a carcinoma of the bladder, breast, colon, kidney, liver, lung, ovary, pancreas, rectum, or stomach; a hematopoietic tumor of lymphoid or myeloid lineage; a tumor of mesenchymal origin such as a fibrosarcoma or rhabdomyosarcoma; or another tumor, including a melanoma, teratocarcinoma, neuroblastoma, or glioma. Preferably, the invention can be used in the treatment of pancreatic cancer. It also is anticipated that the patient can be treated prior to, or in addition to (i.e., concurrently or immediately following) immunotherapy as described herein with any number of methods as are employed to treat cancer, for instance, surgical resection, irradiation, chemotherapy, and the like.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments can be used and that it is intended that the invention can be practiced otherwise than as specifically described herein. Accordingly, this invention includes all modifications encompassed within the spirit and scope of the invention as defined by the following claims.

What is claimed is:

1. A method of stimulating an antitumor immune response to a pancreatic tumor in a mammalian host that has pancreatic cancer, which method comprises:

administering to said mammalian host a pancreatic tumor cell line, which (i) has been derived from a primary pancreatic tumor, (ii) is purified from stromal and noncancerous epithelial cells, (iii) is allogeneic and not major histocompatibility-matched to said mammalian host, and (iv) has been modified so that it produces an increased level relative to the unmodified pancreatic tumor cell line of a cytokine, which stimulates an antitumor immune response, wherein the administration of said pancreatic tumor cell line to said mammalian host stimulates an antitumor immune response to said pancreatic tumor in said mammalian host.

2. The method of claim 1, wherein said pancreatic tumor cell line is administered to said mammalian host in vivo in close proximity to said pancreatic tumor.

3. The method of claim 1, wherein said pancreatic tumor cell line is irradiated prior to administration to said mammalian host.

4. The method of claim 1, wherein said pancreatic tumor cell line is treated to enhance its immunogenicity prior to administration to said mammalian hose.

5. The method of claim 4, wherein said pancreatic tumor cell line is treated by admixture with an adjuvant.

6. The method of claim 1, wherein said pancreatic tumor cell line has been derived from a primary pancreatic tumor by:

(a) obtaining a sample of tumor cells from a primary pancreatic tumor from a mammalian host, (b) forming a single cell suspension from said sample of tumor cells, (c) pelleting tumor cells from said single cell suspension, (d) plating the pelleted tumor cells in a growth medium comprising fetal serum, insulin at a concentration of from about 0.1 to about 1.0 U/ml, and insulin-like growth factor 1 at a concentration of from about 0.005 to about 0.05 µg/ml, and insulin-like growtn factor 2 at a concentration of from about 0.005 to about 0.05 µg/ml, and (e) purifying said tumor cells.

7. The method of claim 1, wherein said pancreatic tumor cell line comprises a mutation in an oncogene or a tumor suppressor gene that allows confirmation of the oncogenic nature of the pancreatic tumor cell line and its derivation from a host tumor.

8. The method of claim 7, wherein said mutation is in a ras gene.

9. The method of claim 1, wherein said cytokine is granulocyte-macrophage colony stimulating factor (GM-CSF).

10. The method of claim 8, wherein said pancreatic tumor cell line comprises a mutation in codon 12, 13 or 61 of H-ras, K-ras or N-ras and expresses cell-surface cytokeratins and high levels of MHC class I antigens.

11. The method of claim 6, wherein said pancreatic tumor cell line is administered to said mammalian host in vivo in close proximity to said pancreatic tumor.

12. The method of claim 6, wherein said pancreatic tumor cell line is irradiated prior to administration to said mammalian host.

13. The method of claim 6, wherein said pancreatic tumor cell line is treated to enhance its immunogenicity prior to administration to said mammalian host.

14. The method of claim 13, wherein said pancreatic tumor cell line is treated by admixture with an adjuvant.

15. The method of claim 6, wherein said pancreatic tumor cell line comprises a mutation in an oncogene or a tumor suppressor gene that allows confirmation of the oncogenic nature of the pancreatic tumor cell line and its derivation from a host tumor.

16. The method of claim 15, wherein said mutation is in a ras gene.

17. The method of claim 6, wherein said cytokine is GM-CSF.

* * * * *